(12) United States Patent
Lamer et al.

(10) Patent No.: US 7,424,679 B1
(45) Date of Patent: Sep. 9, 2008

(54) PATIENT DATA INFORMATION SYSTEM

(75) Inventors: Roland Lamer, Evanston, IL (US);
Atulkishen Venkatesh Setlur, Arlington Heights, IL (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/474,569

(22) Filed: Dec. 29, 1999

(51) Int. Cl.
*G06F 3/00* (2006.01)

(52) U.S. Cl. .................. 715/737; 715/736; 715/764; 705/2; 705/3

(58) Field of Classification Search .......... 345/810, 345/700, 754; 705/2, 3; 715/700, 754, 810, 715/764, 736, 737, 750
See application file for complete search history.

(56) References Cited

U.S. PATENT DOCUMENTS

| | | | | |
|---|---|---|---|---|
| 5,452,416 | A | * | 9/1995 | Hilton et al. ............. 345/161 |
| 5,710,889 | A | | 1/1998 | Clark et al. .............. 705/44 |
| 5,751,286 | A | * | 5/1998 | Barber et al. ............ 345/835 |
| 5,924,074 | A | * | 7/1999 | Evans .................... 705/3 |
| 6,032,120 | A | * | 2/2000 | Rock et al. ............... 705/2 |
| 6,260,021 | B1 | * | 7/2001 | Wong et al. .............. 705/2 |
| 6,556,698 | B1 | * | 4/2003 | Diano et al. ............. 382/132 |

\* cited by examiner

*Primary Examiner*—Weilun Lo
*Assistant Examiner*—Mylinh Tran
(74) *Attorney, Agent, or Firm*—Andrus, Sceales, Starke & Sawall, LLP

(57) ABSTRACT

The patient data information system of the present invention integrates patient image data and patient textual data and provides a method for patient data creation, maintenance and retrieval. The patient data information system comprises a display unit coupled to a workstation with the workstation configured to operate a first software application which is configured to display patient images for a patient on the display unit. The workstation also is configured to work a second software application. When the first software application is configured to generate a patient context for the patient being treated and provide the patient context to the second software application and display patient data from the second software application based on the patient context. The first software application retrieves patient image data from a Picture Archival and Communication System (PACS). And the second software application is configured to retrieve patient textual data from a Radiology Information System (RIS) wherein the patient data includes the patient textual data. A high resolution monitor displays the patient image data and the patient textual data and the user of the present patient data information system retrieves and inputs data utilizing an input unit from a group consisting of a mouse, a voice recognition system, a keystroke on a keyboard, a switch and a light pin. The second software application includes a plurality of RIS applications such as a case sign out application, a report entry application, an order detailing the application and an order viewer application.

23 Claims, 6 Drawing Sheets

PathSpeed Extend Framework

Figure 5

PATIENT DATA INFORMATION SYSTEM

FIELD OF THE INVENTION

This invention relates to medical records management systems, and more particularly to a patient data information system to integrate a Picture Archival and Communication System with a Radiology Information System on a single workstation.

BACKGROUND OF THE INVENTION

Medical scanners and medical imaging machines are an integral part of modern medical practice. The scanners and medical imaging devices utilize both electromagnetic radiation and sonic wave to produce images which are viewed by doctors for the diagnosis and care of patients. For example, ultrasound machines are useful for viewing fetuses during prenatal care in a pregnancy or blood flow patterns in arteries. Magnetic resonant imaging machines are useful for producing images in a wide variety of soft tissues. Computer tomology imaging machines are useful for producing images of scalable structures.

In a hospital, medical scanners and medical imaging devices are preferably networked with a central image management system such as a Picture Archival and Communications System (PACS). The PACS is designed to provide a central storage for archive of medical images. Further, PACS is configured so that stored images may be retrieved. Typically, a hospital will have a single PACS that is networked with a plurality of medical scanners and medical imaging devices located throughout the hospital. Further, the PACS will be networked with a plurality of image workstations, such as a PACS workstation. Images generated by medical scanners and medical imaging devices are transferred to the PACS for storage and later retrieval and review by doctors located throughout the hospital at any of the plurality of image workstations.

Also in a hospital, medical scanners and medical imaging devices are coupled to a Radiology Information System (RIS). The RIS is designed to provide a central storage for archive of patient textual data as well as information relating to the medical procedures, reports, medical orders, test results, patient demographics, etc. Further, RIS is configured so that stored textual information may be retrieved by a user. Typically, a hospital will have a single RIS that is networked with a plurality of workstations located throughout the hospital. Patient information generated at these workstations by users, such as radiology technicians, nurses, radiologists, and physicians, are transferred to the RIS for storage and later retrieval and review by radiologists located throughout the hospital at any of the plurality of RIS workstations.

A conventional PACS system and a RIS system, as explained above, are completely separate and distinct systems. Each system duplicates many of the components in each system thereby increasing the capital expenditure costs and maintenance expenses incurred by the hospital. Typically, an information exchange bridge referred to as a PACS broker, which links the two systems, can be used, but a radiologist must still access image data from the separate PACS workstation and patient textual data from the separate RIS workstation. In other words, the radiologist must have two separate workstations readily available in order to review patient images and patient textual data to completely diagnose a patient.

Thus, there is a need for a patient data information system that integrates the patient image data and patient textual data on a single workstation. There is a further need for a patient data information system that allows the user to access patient image data and patient textual data, manipulate such data as is necessary for treatment and enter new data concerning such patient treatment in a single workstation. In addition, there is a need for a patient information system that is accessible by a plurality of users that can retrieve and input data, either textual data or image data, simultaneously.

SUMMARY OF THE INVENTION

The patient data information system of the present invention integrates patient image data and patient textual data and provides a method for patient data creation, maintenance and retrieval. The patient data information system comprises a display unit coupled to a workstation with the workstation configured to operate a first software application which is configured to display patient images for a patient on the display unit. The workstation also is configured to work a second software application. When the first software application is configured to generate a patient context for the patient being treated and provide the patient context to the second software application and display patient data from the second software application based on the patient context. The first software application retrieves patient image data from a Picture Archival and Communication System (PACS). And the second software application is configured to retrieve patient textual data from a Radiology Information System (RIS) wherein the patient data includes the patient textual data. A high resolution monitor displays the patient image data and the patient textual data and the user of the present patient data information system retrieves and inputs data utilizing an input unit from a group consisting of a mouse, a voice recognition system, a keystroke on a keyboard, a switch and a light pin. The second software application includes a plurality of RIS applications such as a case sign out application, a report entry application, an order detailing the application and an order viewer application.

Another embodiment of the patient data information system comprises a second workstation coupled to the workstation with the second workstation configured to operate the second software application. The two workstations are coupled via an object request broker with a bridge coupled between the second workstation and the object request broker. The bridge provides a communication path for translating a Component Object Model (COM) software and a common object request broker architecture software.

The patient data information system of the present invention also provides a method of integrating patient data from first and second applications comprising displaying a first set of patient data using the first application and generating a patient context for that patient. The patient context from the first application is provided to a second application and a second set of patient data from the second application is displayed. The method also includes retrieving the first set of patient data from an image data base and retrieving a second set of patient data from a Radiology Information System. The step of providing further includes generating an event based on a patient context and providing the event to the second application for further processing. The method also includes converting the event obtained from a first object model to a second object model and providing the converted event to the second application.

BRIEF DESCRIPTION OF THE DRAWINGS

FIG. 5 is an example of an annotated window of the monitor of the PACS workstation displaying patient data according to an exemplary embodiment;

DETAILED DESCRIPTION OF THE PREFERRED EMBODIMENTS

Figure 1:
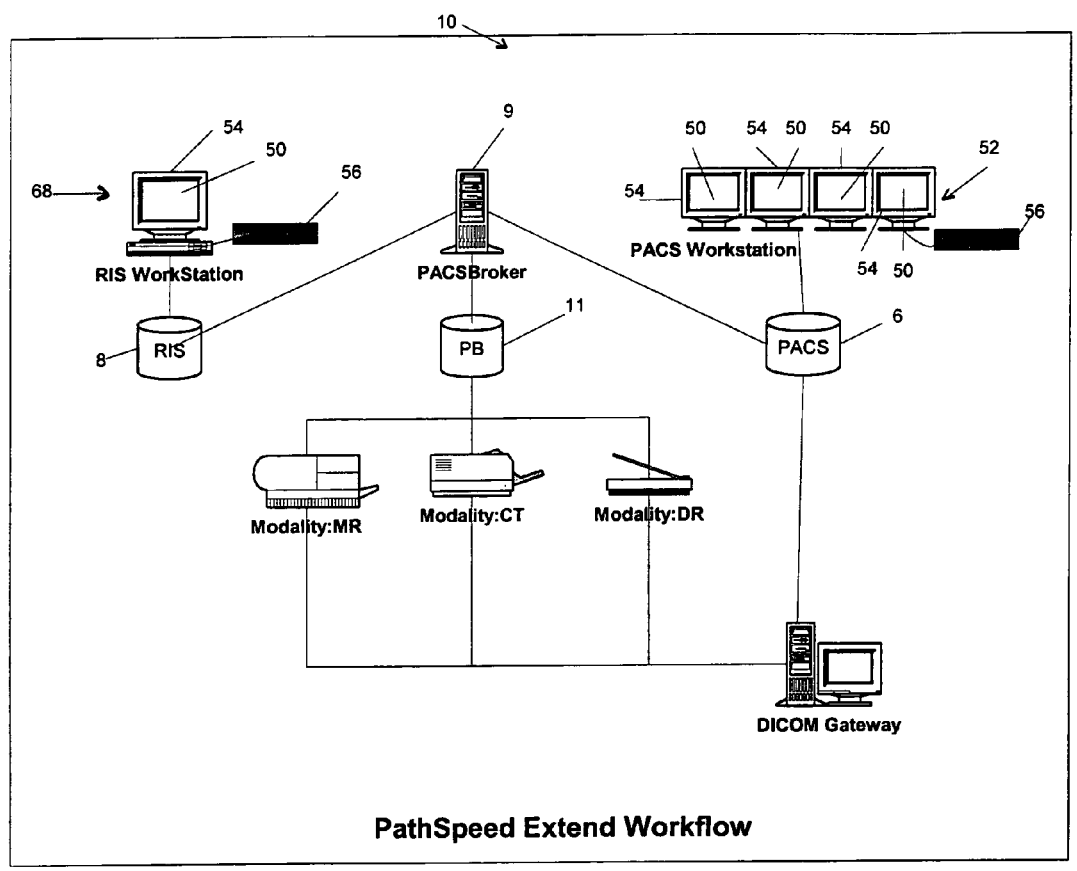
FIG. 1 is an illustration of a PACS workstation and its associated data base containing the present patient data information system according to an exemplary embodiment interconnected through a PACS broker to a RIS workstation and its associated data base with a plurality of modality types providing patient image and textual data to the respective RIS and PACS databases through the PACS broker in a DICOM gateway.

Referring to FIG. 1, there is illustrated an exemplary embodiment of a patient data information system (10). A workstation (52) has a display unit (50), which can include a plurality of monitors (54), coupled to a Picture Archival and Communication System (PACS) and associated PACS data base (6). The data base (6) associated with workstation (52) is in communication with a PACS broker (9) which allows communication between the data base of workstation (52) and a second data base (8) associated with a second workstation (68) and provides access to a Radiology Information System (RIS) and its associated RIS data base (8). The workstations (52) and (68) are also provided with an input unit (56). The input unit (56) can include one or more of a mouse, a voice recognition system, a keyboard keystroke assembly, a switch, and a light pen for inputting and retrieving information from the particular workstation.

The patient data information system (10) provides for integration between the applications residing on workstation (52) and third party applications residing on the same workstation or the network to which the workstation is coupled to improve work flow and productivity of patient data information. During the treatment of a patient (P) a user, typically a radiologist, will log into a workstation to obtain patient information, usually textual data as well as image data. The user will manipulate or use that information and provide additional input based on observation and analysis relating to the treatment and care of the patient based on the patient data made available on the information system. The present patient data information system (10) integrates the patient image data with the patient textual data on the same workstation. The present patient data information system (10) provides the communication mechanism that allows different applications residing on the workstation or on the network to which the workstation is attached to share the context information. The system (10) includes a conduit that allows two-way patient context exchanges between the multiple applications residing on the same workstation or the same workstation network. The patient context includes, for example, patient identification data, user identification data and patient examination information, etc. Patient data is obtained by inputting data, either textual or image data from the various modalities to which a patient is subjected during a medical treatment. Such modalities can include magnetic resonance imaging (MRI) devices or ultrasound or computer tomology imaging (CT) devices or it can include data inputted with a word processing application. Such patient data is stored in either the RIS data base (8) or the PACS data base (6) either directly through the PACS broker data base (11) or through a DICOM gateway.

Figure 2:
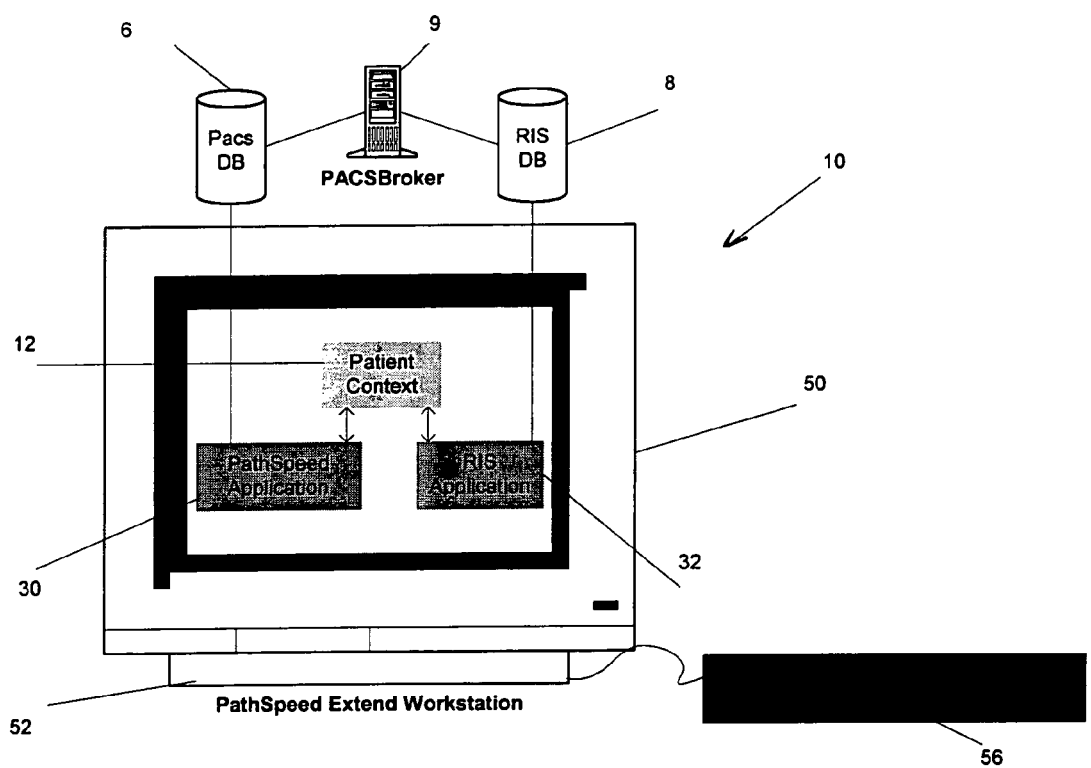
FIG. 2 is an illustration of the PACS workstation displaying PACS application information on the workstation monitor together with RIS application information displayed on the same monitor with the patient context being transmitted from one application to another in the background, according to an exemplary embodiment.

Referring now to FIG. 2, the present patient data information system (10) comprises a display unit (50) which can include one or more high resolution monitors (54) (shown in FIG. 1) coupled to a workstation (52). The workstation (52) is configured to operate a first software application (30) configured to display patient images, for a patient (P), on the display unit (50) upon request by a user via an input unit (56) coupled to the workstation (52). The first application (30) is configured to generate a patient context (12) for the patient (P) and provide the patient context (12) to a second software application (32). The second application (32) displays patient data from the second application (32) based on the patient context (12). In this exemplary embodiment, the first application (30) is configured to retrieve patient image data from a Picture Archival and Communication System (PACS) database (6) and the second application (32) is configured to retrieve patient textual data from a Radiology Information System (RIS) data base (8) wherein the patient data includes the patient textual data. As is mentioned above, the display unit (50) includes a monitor (54) (shown in FIG. 1) having a resolution of at least 90 dots per inch (dpi).

During the process of operating the patient data information system (10) the second application (32) is, for example, an RIS application, such as, a case sign out application, a report entry application, an order detailing application, an order viewer application, etc. Such applications are invoked by activating a command such as by "clicking" on an icon displayed in a graphic user interface on the monitor (54) (shown in FIG. 1) of the display unit (50) of the workstation (52) as determined by the user of the patient data information system (10). The procedure can also be invoked by the user utilizing an input unit (56), for example, a mouse, a voice recognition system, a keyboard stroke, a switch, and a light pen, etc.

Upon logging onto the workstation (52) or at another time during operation of system (10), a patient context (12) is created. The patient context (12) includes the patient identification data such as name, address, age, social security number, etc., associated with a specific and particular patient (P). The patient context can also include user identification data such as the name, password, etc., of the user of the patient data information system (10). In addition, the patient data includes patient examination information such as ordered tests, test results, test analysis, prognosis, diagnostic information relating, etc., to that specific and particular patient (P). The first application (30) shares the patient context (12) with the second application (32). In the preferred embodiments the first application (30) is in communication with the PACS data base (6) and the second application (32) is in communication with the RIS data base (8), which databases (6, 8) are interconnected to the PACS broker (9).

Figure 3:
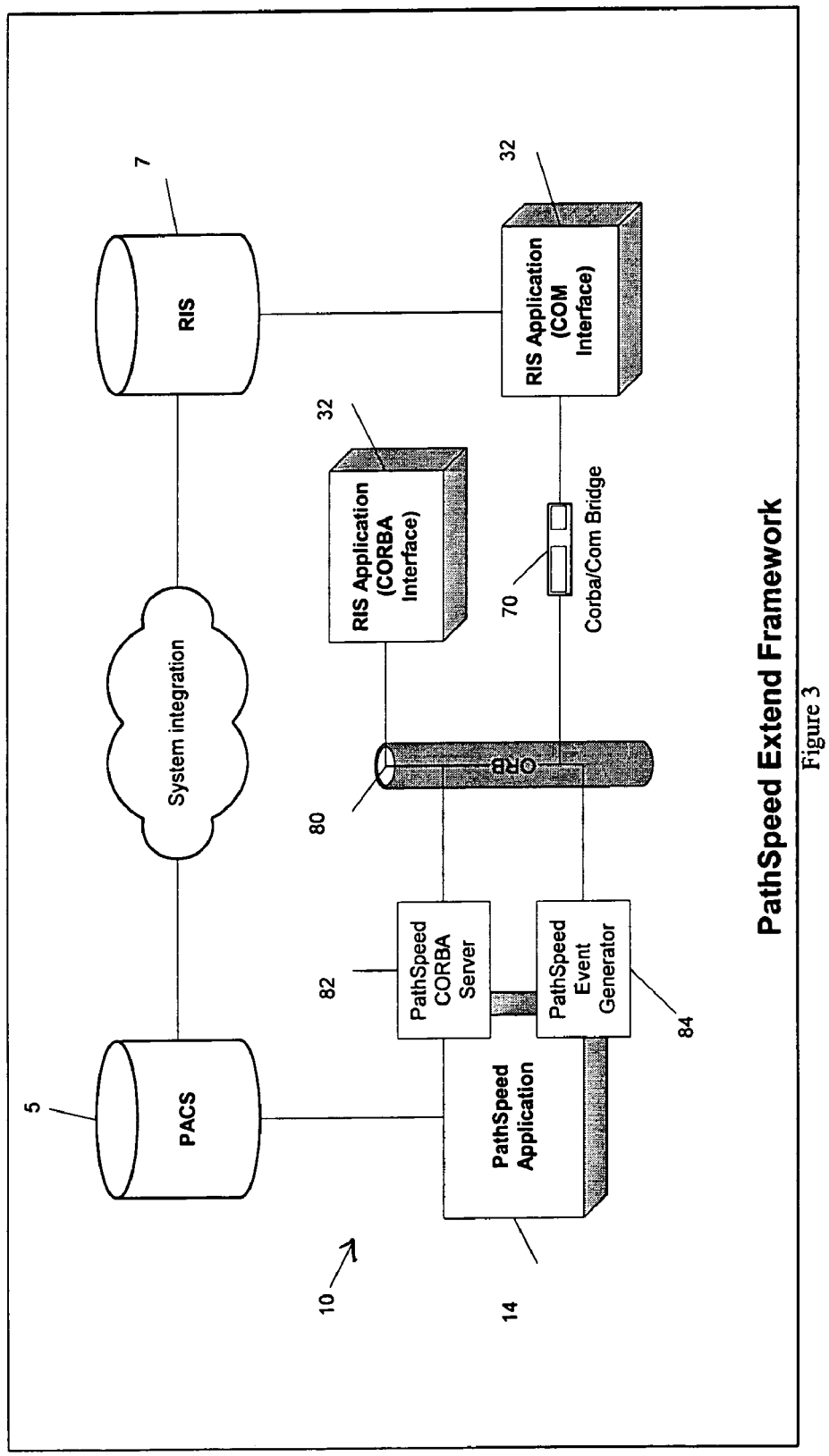
FIG. 3 is a block diagram illustrating the patient information data system architecture according to an exemplary embodiment.

Referring to FIGS. 1 and 3, another embodiment of the patient data information system (10) includes a second workstation (68) coupled to the workstation (52) with the second workstation (68) configured to operate the second application (32). An object request broker (80) allows the software application on one workstation to communicate with another software application operating on the second workstation or to communicate with two applications on the same workstation. To further facilitate the communication between two applications, a bridge (70) is coupled between the second workstation (68) and the object request broker (80) wherein the second application (32) operating on the second workstation (68) communicates with the first workstation (52) via a Component Object Model (COM). The Component Object Model is a Microsoft Corporation specification which is binary compatible with a C++ compiler v-table generator which facilitates basic C++ classes. In operation, the first application (30) preferably is accessing and manipulating patient image data (16). A CORBA server (82) is a CORBA based interface to allow the first application to interface and communicate with other applications operating on the system. CORBA is a common object request broker architecture specification adopted by software developers that uses an object orientated approach to create reusable software components. The CORBA server (82) creates an object in accord with the specification and upon which operations can be invoked by the first application. The objects created by the CORBA server (82) correspond to certain actions that can be performed by the first application (30). In an event generator (84) operated with the first application is an event suite that is used to send notification of what the first application (30) is currently or has finished processing. The common object request broker architecture is used to implement the communication layer between the several applications operating on the patient data information system (10). The common object request broker architecture provides an infrastructure that enables invocations of operations on objects created by the CORBA located anywhere on the network to which the workstation (52) is connected as if that object was on the local workstation (52). The object request broker (80) facilitates the communication between the first application (30) and the second application (32). If the second application (32), typically the patient textual data (18) of a RIS data base (8), is created by CORBA a direct communication with the second application is available through the object request broker (80). If the patient textual data (18) on the RIS data base (8) is created by the component object model a bridge (70) must then be invoked to translate between the component object model and the common object request broker architecture. This COM/CORBA bridge allows bi-directional messaging between objects written using CORBA and those written using COM. The bridge does the conversion between the two distributed objects in a seamless manner from the point-of-view of the user of the patient data information system (10).

Figure 4:
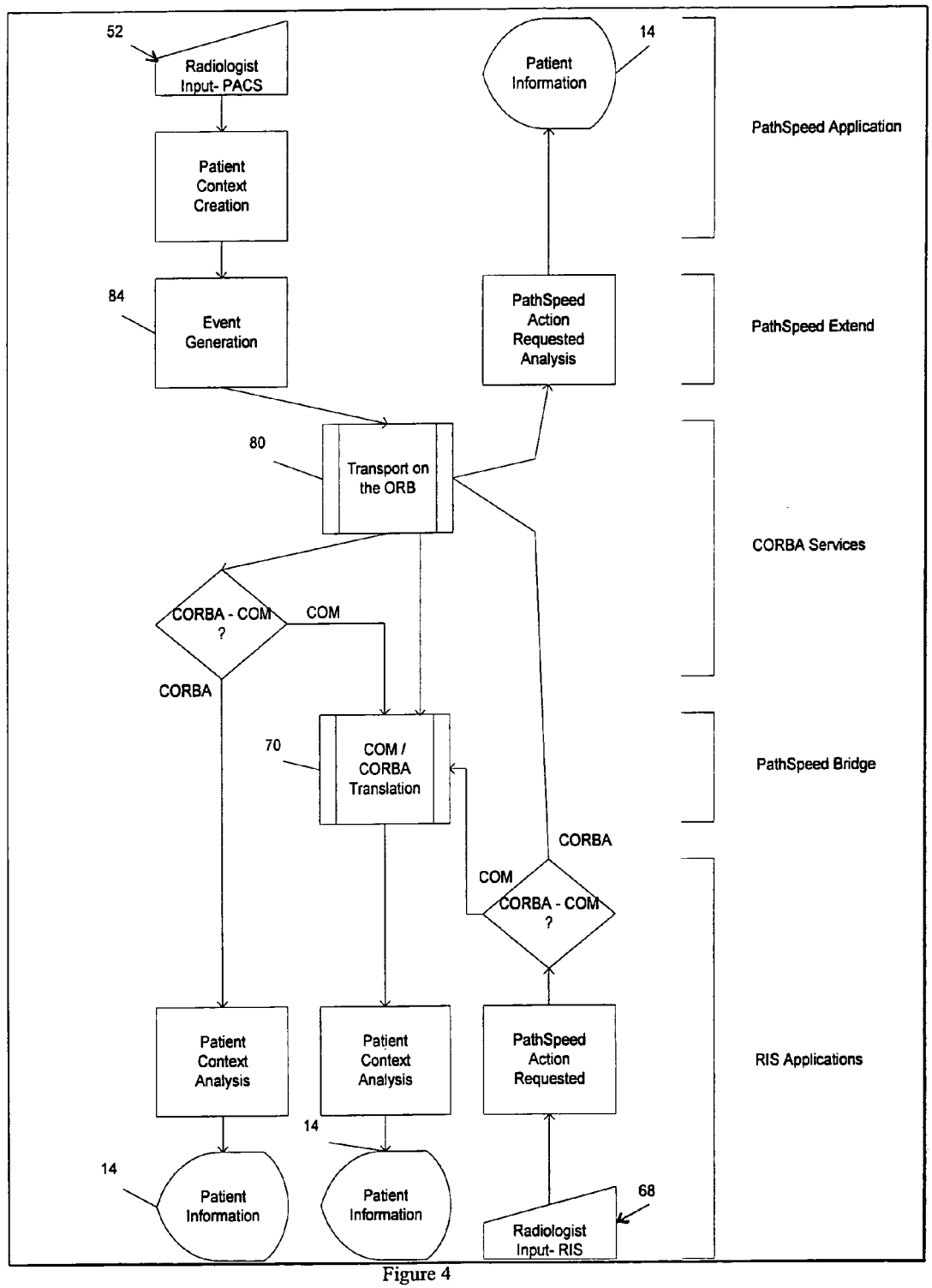
FIG. 4 is a flow chart illustrating the process flow of the patient data information system according to an exemplary embodiment.

Referring to FIG. 4, there is shown a flow chart of the integration process of the present patient data information system (10). A user logs onto the system at either the PACS workstation (52) or the RIS workstation (68) utilizing a user interface displayed on the monitor (52) of the display unit (50) of the workstation. Upon such login, a patient context (12) is created. The patient context (12) object is wrapped into an event by the event generator (84) and sent to the second application (32), typically the RIS application via the object request broker (80). If the RIS application is CORBA enabled it will receive and analyze the event and display the pertinent patient information based on the received patient context (12). If the RIS application is COM enabled, the event is translated from COM to CORBA using the bridge (70). A similar procedure is provided if the initiating logon occurs at a RIS workstation (68).

Figure 5:
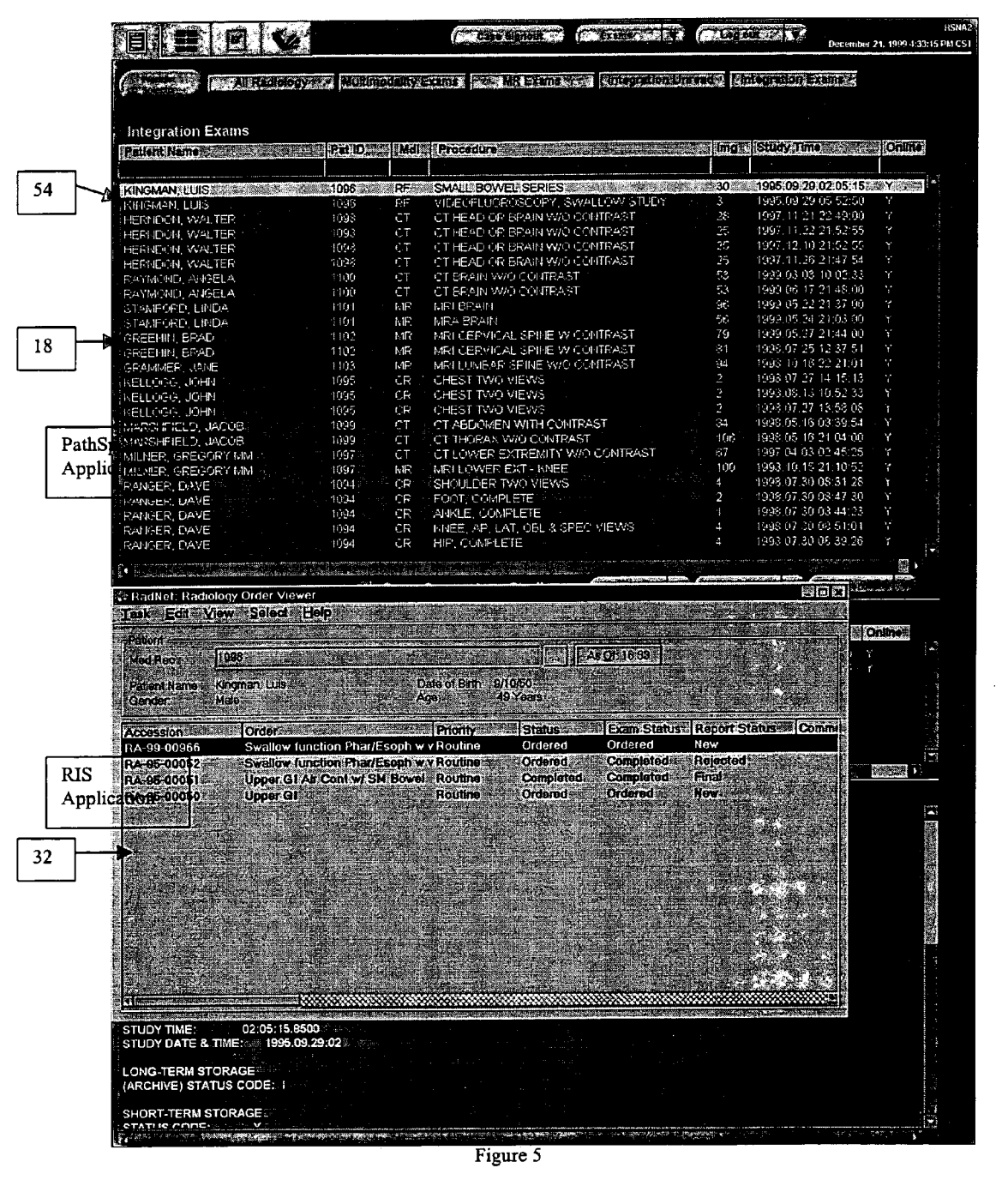

FIG. 5 is an example of a monitor screen on a workstation in the present patient data information system (10) displaying patient textual data (18) from a first application (30) and patient textual data (18) from a second application (32). The first application (30) in the illustration is from a PACS data base (6) and the second application (32) data is from a RIS data base (8).

Figure 6:
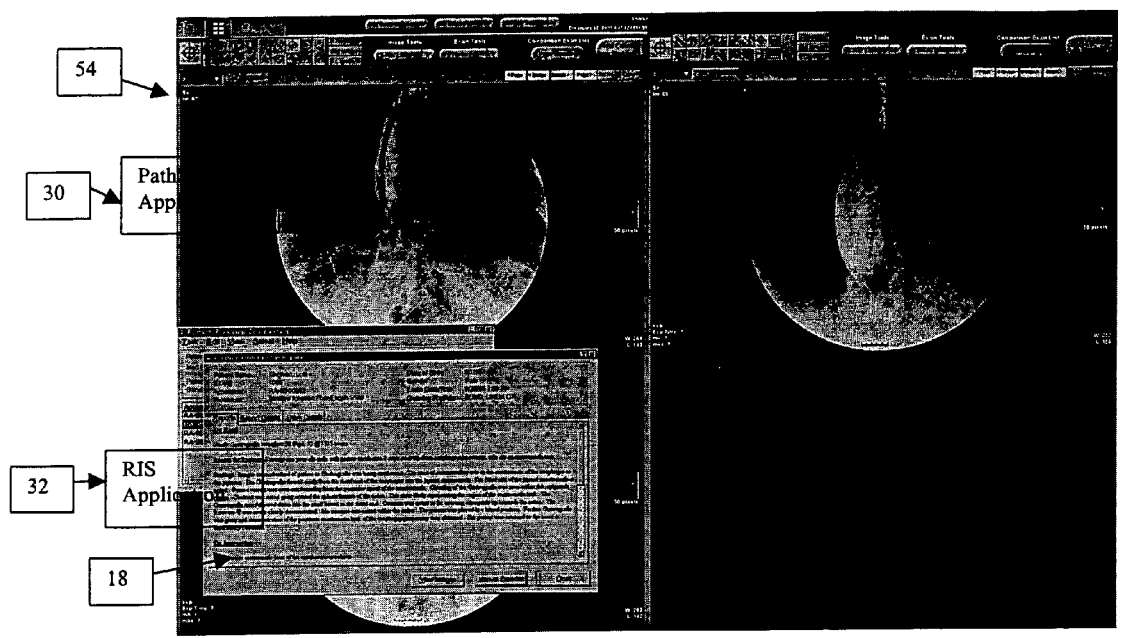
FIG. 6 is an example of an annotated window of the patient data information system displaying patient image data and patient textual data according to an exemplary embodiment.

FIG. 6 is an example of a screen on a monitor (54) of a workstation display unit (50). The first application (30) is displaying patient image data (16) and the second application (32) is displaying patient textual data (18).

Thus, there is provided a patient data information system that integrates patient data including patient image data and patient textual data in a patient context on a single workstation. While several embodiments of the present invention have been disclosed and described in detail herein, various modifications may be made. For example, the preferred embodiment of the patient data information system was described in a Microsoft Corporation Windows NT environment. Other networking operating systems can also be used to integrate the patient image data and patient textual data in a seamless fashion on a single workstation. By way of further modification, the communication between workstations, the PACS broker and the PACS and RIS data bases, can be facilitated by a wireless communication system or by an optical link communication system. Such modifications and variations in use are intended to fall within the scope of the appended claims.

What is claimed is:

1. A patient data information system, comprising:
a display unit;
a first application configured to display patient images for a patient on the display unit, wherein the first application is configured to retrieve patient image data from a picture archival and communication system (PACS) and to automatically extract and generate a set of patient context data for the patient from the retrieved patient image data, and further wherein the set of patient context data includes patient and user information;
a second application configured to retrieve a set of patient textual data from a radiology information system (RIS); and
a workstation coupled to the display unit and configured to operate both the first application and the second application that reside on the workstation, the first application configured to send the automatically extracted and generated set of patient context data to the second application after the patient image data is retrieved, and the second application configured to receive the set of patient context data from the first application and to retrieve and display the set of patient textual data on the display unit in response to the retrieval of the patient image data and extraction and generation of the set of patient context data.

2. The patient data information system of claim 1, wherein the display unit includes a monitor having a resolution of at least 90 dpi.

3. The patient data information system of claim 1, wherein the second application is selected from the group consisting of a case signout application, a report entry application, an order detailing application, and an order viewer application.

4. The patient data information system of claim 1, further comprising a second workstation coupled to the workstation, the second workstation configured to operate the second application.

5. The patient data information system of claim 1, wherein the second application is coupled to the first application via an object request broker.

6. The patient data information system of claim 5, further comprising a bridge coupled between the second application and the object request broker, wherein the second application communicates via the component object model (COM).

7. The patient data information system of claim 1, further comprising an input unit, the first application generating the set of patient context data in response to user input at the input unit.

8. The patient data information system of claim 7, wherein the input unit is selected from the group consisting of a mouse, a voice recognition system, a keystroke, a switch, and a light pen.

9. The patient data information system of claim 1, wherein the patient data includes patient examination information.

10. A method of integrating patient data from first and second applications residing on a single workstation, comprising:
    displaying patient images retrieved from an image database using the first application on the workstation, wherein the first application is configured to retrieve patient image data from a picture archival and communication system (PACS);
    extracting and generating a set of patient context data for a patient using the first application, wherein the set of patient context data is automatically extracted and generated from the retrieved patient image data and includes patient and user information;
    sending the set of patient context data from the first application to the second application on the workstation;
    retrieving a set of patient textual data based on the set of patient context data using the second application, wherein the second application is configured to retrieve the set of patient textual data from a radiology information system (RIS); and
    displaying the set of patient textual data using the second application on the workstation.

11. The method of claim 10, wherein the step of sending includes generating an event based on the set of patient context data and providing the event to the second application.

12. The method of claim 11, further comprising converting the event from a first object model to a second object model and providing the converted event to the second application.

13. The method of claim 10, wherein the second application is selected from the group consisting of a case signout application, a report entry application, an order detailing application, and an order viewing application.

14. The method of claim 10, further comprising receiving an operator input from an input unit and generating the set of patient context data for the patient in response to the operator input.

15. The method of claim 10, wherein the set of patient data includes patient examination information.

16. An apparatus for integrating patient data from first and second applications residing on a single workstation, comprising:
    a means for displaying patient images retrieved from an image database using the first application on the workstation, wherein the first application is configured to retrieve patient image data from a picture archival and communication system (PACS);
    a means for extracting and generating a set of patient context data for a patient using the first application, wherein the set of patient context data is automatically extracted and generated from the retrieved patient image data and includes patient and user information;
    a means for sending the set of patient context data from the first application to the second application on the workstation;
    a means for retrieving a set of patient textual data based on the set of patient context data using the second application, wherein the second application is configured to retrieve the set of patient textual data from a radiology information system (RIS); and
    a means for displaying the set of patient textual data using the second application on the workstation.

17. The apparatus of claim 16, wherein the means for sending includes a means for generating an event based on the set of patient context data and providing the event to the second application.

18. The apparatus of claim 17, further comprising a means for converting the event from first object model to a second object model and a means for providing the converted event to the second application.

19. The apparatus of claim 16, wherein the second application is selected from the group consisting of a case signout application, a report entry application, an order detailing operation, and an order viewer application.

20. The apparatus of claim 16, further comprising a means for receiving an operator input and generating the set of patient context data for the patient in response to the operator input.

21. The apparatus of claim 16, wherein the set of patient data includes a means for providing patient examination information.

22. A patient data information workstation, comprising:
    a display;
    a first application configured to retrieve and display patient images for a patient on the display, wherein the first application is configured to retrieve patient image data for a picture archival and communication system (PACS), and further configured to automatically extract and generate a set of patient context data associated with the patient when patient image data is retrieved, and further wherein the set of patient context data includes patient and user information; and
    a second application configured to receive the set of patient context data sent from the first application and to retrieve and display a set of patient textual data for the patient on the display in response to the retrieval of the patient image data and extraction and generation of the set of patient context data, and further wherein the second application is configured to retrieve the set of patient textual data from a radiology information system (RIS).

23. A patient data information workstation according to claim 22, further including a third application in data communication with the first application, the third application configured to receive the set of patient context data sent from the first application and to retrieve and display patient data for the patient based on the set of patient context data.

* * * * *